United States Patent [19]

Morrissey et al.

[11] Patent Number: 5,394,889
[45] Date of Patent: Mar. 7, 1995

[54] APPARATUS AND METHOD FOR CONTROLLING HUMAN LACTATION

[76] Inventors: Suzanne E. Morrissey; Gerald Morrissey, both of 3 Lake View Cir., Skaneateles, N.Y. 13152

[21] Appl. No.: 954,012

[22] Filed: Sep. 30, 1992

[51] Int. Cl.⁶ .............................................. A61G 15/00
[52] U.S. Cl. .................................. 128/845; 128/890
[58] Field of Search ............... 128/890, 889; 2/1, 2; 604/366, 370, 377, 378, 381, 383; 450/36, 37, 38, 39, 40, 41, 47, 57, 63, 68, 72, 80, 81, 86–88

[56] References Cited

U.S. PATENT DOCUMENTS

| | | | |
|---|---|---|---|
| 1,671,342 | 5/1928 | Cantor | 128/858 |
| 2,834,352 | 5/1958 | Ullian | 450/57 |
| 2,891,544 | 6/1959 | London | 450/37 |
| 4,333,471 | 6/1982 | Nakai | 128/890 |
| 4,566,458 | 1/1986 | Weinberg | 128/890 |
| 4,870,977 | 10/1989 | Imonti | 128/890 |
| 4,875,492 | 10/1989 | Mitchell | 128/890 |
| 5,032,103 | 7/1991 | Larsson | 128/890 |

FOREIGN PATENT DOCUMENTS

| | | | |
|---|---|---|---|
| 1133702 | 4/1957 | France | 128/890 |
| 0337643 | 6/1921 | Germany | 128/890 |
| 0177295 | 3/1922 | United Kingdom | 128/890 |

OTHER PUBLICATIONS

*The Womanly Art of Breastfeeding* 78 (4th Ed. 1987), published by the La Leche League International.

*Primary Examiner*—Michael A. Brown
*Attorney, Agent, or Firm*—Nixon, Hargrave, Devans & Doyle

[57] ABSTRACT

An apparatus having a support having an outer surface and an inner surface that is shaped to conform substantially to a human female breast and having a protrusion which extends away from the support and is positioned to align substantially with and contact a nipple of a human female breast prevents a human female breast from lactating when placed over the breast. The present invention also provides a method for controlling human lactation which utilizes the present apparatus and includes the steps of placing and positioning the apparatus over the breast and applying pressure on the apparatus sufficient to prevent lactation.

18 Claims, 1 Drawing Sheet

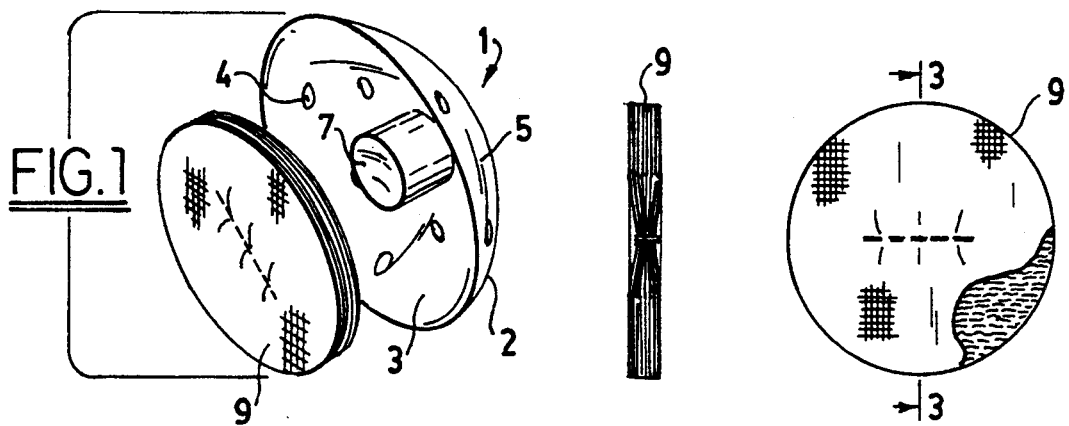
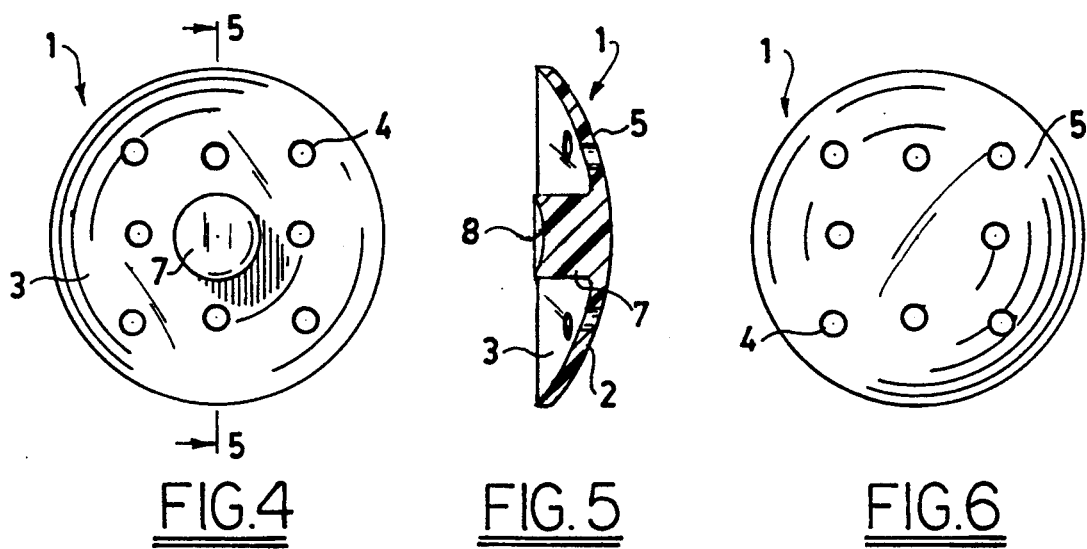
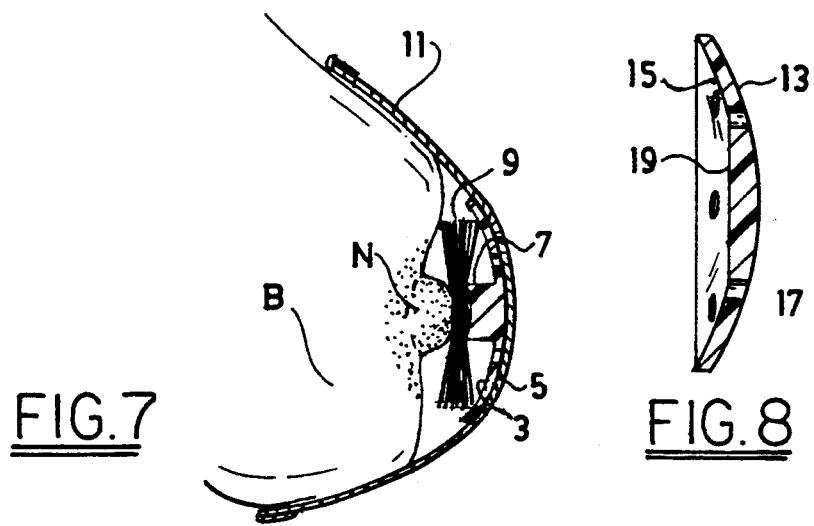

APPARATUS AND METHOD FOR CONTROLLING HUMAN LACTATION

FIELD OF INVENTION

The present invention relates to an apparatus and method for controlling lactation in human females.

BACKGROUND OF THE INVENTION

In recent years, breast feeding of newborn babies has seen a resurgence in popularity. Breast feeding is becoming more popular for a variety of reasons relative to both baby and mother. These advantages include increased protection of the infant from illness through the development of protective antibodies, decreased risk of developing childhood cancers, avoiding potential allergies to commercial infant formulas, and enhanced jaw, teeth, and speech development, among others. Furthermore, it has been suggested that nursing mothers have a lower risk of developing breast cancer. Breast feeding has also been suggested to improve the emotional bond between mother and child.

Although breast feeding is enjoying renewed use, it is not without disadvantages. The outpouring of milk is known as the "let-down" or "milk-ejection" reflex. A let-down can occur several times during a feeding. It is well known that the milk-ejection reflex can be triggered at inappropriate times by various stimuli. A baby's crying, for example, may cause let-down in a nursing mother. This can result in let-down at very inopportune times.

This inappropriate let-down can be particularly problematic for working mothers who are nursing. Solutions designed to alleviate problems associated with inappropriate let-down include absorbent breast pads or breast shields that operate, essentially, as a well or reservoir to collect leaking milk. These solutions are disadvantageous because of the limited capacity of both types of devices as well as the likelihood that milk will leak into clothing despite their use.

It is also known that nursing mothers can apply direct pressure to the nipples with the heels of their hands or forearms to temporarily halt leakage. However, this type of solution likewise presents obvious disadvantages for the nursing mother who is working or otherwise in public. Therefore, there continues to be a need for apparatus that can effectively control inopportune lactation in nursing mothers.

SUMMARY OF THE INVENTION

This invention relates to an apparatus and method for controlling human lactation. The apparatus comprises a support having an outer surface and an inner surface that is shaped to conform substantially to a human female breast. The inner surface has a protrusion which extends away from the support and is positioned to align substantially with and contact a nipple of a human female breast when the apparatus is placed over the breast. In this way, the protrusion substantially prevents the breast from lactating.

The apparatus can be used alone or include a brassiere which the support is either placed into or integrated with (e.g., sewn into). The brassiere can be either a conventional or nursing brassiere.

The present invention also provides a method for controlling human lactation which utilizes the present apparatus. The method includes the steps of placing the apparatus over the breast and applying pressure on the apparatus sufficient to prevent lactation.

The apparatus and method of the present invention provide a convenient and effective way to prevent inopportune milk leakage in the nursing mother. The apparatus can be inexpensively constructed in a variety of shapes from a variety of materials.

BRIEF DESCRIPTION OF THE DRAWINGS

FIG. 1 is an exploded, perspective view of one embodiment of the apparatus of the present invention and an absorbent breast pad.

FIG. 2 is a front View of an absorbent breast pad.

FIG. 3 is a side view of an absorbent breast pad.

FIG. 4 is a perspective view of the inner surface and protrusion of the present apparatus.

FIG. 5 is a cross-sectional side view of FIG. 4 taken along line 5—5.

FIG. 6 is a perspective view of the outer surface of the support of the present apparatus.

FIG. 7 is a cross-sectional side view of the present apparatus, including a brassiere, placed over a human female breast.

FIG. 8 is a is a cross-sectional side view of an alternative embodiment of the inner surface of the support and protrusion of the present invention

DETAILED DESCRIPTION OF THE INVENTION

FIG. 1 is an exploded, perspective view of one embodiment of the apparatus of the present invention and an absorbent breast pad. Apparatus 1 includes support 2 having an inner surface 3 and an outer surface 5. Inner surface 3 has a protrusion 7 which extends away from support 2. Referring to FIG. 7, which is a cross-sectional side view of one embodiment of the present apparatus, including a brassiere, placed over a human breast, protrusion 7 is positioned to align substantially with and contact nipple N of human female breast B. Protrusion 7 operates to depress nipple N, whereby breast B is prevented from lactating.

Support 2 is shaped to conform substantially to a human female breast. Support 2 can, for example, be substantially circular with a concave/convex shape covering a relatively small area of breast B as shown in FIG. 7. Support 2 can also take a variety of other forms, substantially conforming to larger or smaller areas of breast B. Preferably, support 2 is constructed in a substantially circular, concave/convex form and having a radius from about 3 to 5 inches for maximum comfort and to allow use of the apparatus on breasts of various sizes. Most preferably, support 2 is shaped such that suction is created between breast B and apparatus 1 after apparatus 1 is placed over breast B. The suction helps to maintain the alignment of apparatus 1 with nipple N.

Support 2 can be made from a variety of flexible materials including moldable plastic or rubber. Preferably, the support is made from a moldable, flexible plastic material to allow maximum comfort and ease of manufacture. With reference to FIGS. 4 and 6, perspective views of the inner and outer surfaces, respectively, of support 2, support 2 can be provided with holes 4 to allow air circulation around the nipple and areolar region of breast B to prevent local irritation which commonly occurs in nursing mothers.

Protrusion 7 can be produced separately and then attached to inner surface 3 or, preferably, integrated with inner surface 3. This preferred embodiment is shown by FIG. 5, a cross-sectional side view of FIG. 4 taken along line 5—5. Protrusion 7 can be integrated with inner surface 3 by molding protrusion 7 and support 2 together from the same material. Protrusion 7 can be made from a variety of materials, as long as the material is sufficiently rigid to depress nipple N when nipple N is contacted by protrusion 7. Exemplary materials for forming protrusion 7 include any of the rigid plastics known in the art or sufficiently rigidized rubber.

Protrusion 7 can be any shape, so long as it is capable of depressing nipple N when apparatus 1 is brought into contact with breast B and, in turn, preventing lactation. For example, protrusion 7, can be a flattened, planar surface formed in the center of the inner surface 3 of support 2, as shown by FIG. 8, a cross-sectional side view of an alternative embodiment of the inner surface of the support and protrusion of the present invention. Protrusion 7 is preferably cylindrical, having a size approximating a human female nipple, as shown in FIG. 7. Most preferably, as illustrated by FIGS. 7 and 9, nipple-contacting surface 8 of protrusion 7 is concave to make the apparatus more comfortable for the wearer and aid in keeping apparatus 1 in place.

Preferably, absorbent pad 9 is placed over inner surface 3 to absorb any small amount of leakage resulting, for example, from misalignment of protrusion 7 and nipple N. This embodiment is illustrated by FIGS. 1 and 7.

As shown by FIG. 7, the above-described apparatus can be used by placing it over breast B and applying pressure to the apparatus sufficient to depress and, in turn, prevent milk release by nipple N of breast B. The amount of pressure need not be great and can normally be produced by the force provided when apparatus 1 further comprises brassiere 11. Support 2 can be placed inside the cup of brassiere 11 which is then put on by the lactating woman, as illustrated by FIG. 7. Support 2 can either be manually placed into or actually integrated with (e.g., sewn into) the cup of the brassiere. Brassiere 11 can be a conventional or nursing brassiere commonly worn by nursing mothers.

Although the invention has been described in detail, for the purpose of illustration, it is understood that such detail is for that purpose and variations can be made therein by those skilled in the art without departing from the spirit and scope of the invention which is defined by the following claims.

What is claimed is:

1. An apparatus for the control of human lactation comprising a support having an outer surface and an inner surface that is shaped to conform substantially to a human female breast, said inner surface having a protrusion with a concave nipple-contacting surface extending away from said support and positioned to align substantially with and contact a nipple of said human female breast when said apparatus is placed over said human female breast, whereby said protrusion substantially prevents said human female breast from lactating.

2. An apparatus according to claim 1, wherein said outer surface is convex and said inner surface is concave.

3. An apparatus according to claim 1, wherein said protrusion is substantially the same size as said nipple.

4. An apparatus according to claim 1, wherein said protrusion is substantially larger than said nipple.

5. An apparatus according to claim 1, wherein said support is constructed from a flexible material.

6. An apparatus according to claim 5, wherein said flexible material is a plastic.

7. An apparatus according to claim 1 further comprising a brassiere having a cup, wherein said support is placed in side the cup of said brassiere.

8. An apparatus according to claim 7, wherein said brassiere is a conventional brassiere.

9. An apparatus according to claim 7, wherein said brassiere is a nursing brassiere.

10. An apparatus according to claim 1, further comprising an absorbent breast pad placed on said inner surface of said support.

11. An apparatus according to claim 1, wherein said apparatus further comprises a brassiere with which said support is integrated.

12. An apparatus for the control of human lactation comprising a flexible support having an outer convex surface and an inner concave surface that is shaped to conform substantially to a human female breast, said inner surface having a concave protrusion extending away from said support and positioned to align substantially with and contact a nipple of said human female breast when said apparatus is placed over said human female breast, whereby said protrusion substantially prevents said human female breast from lactating.

13. A method for controlling human lactation comprising the steps of:
 providing an apparatus comprising a support having an outer surface and an inner surface that is shaped to conform substantially to a human female breast, said inner surface having a protrusion with a concave nipple-contacting surface extending away from said support and positioned to align substantially with and contact a nipple of said human females breast when said apparatus is placed over said human female breast, whereby said protrusion substantially prevents said human female breast from lactating;
 placing said apparatus over said breast;
 positioning said apparatus to align said protrusion substantially with and contact said nipple of said breast; and
 applying pressure to said apparatus sufficient to prevent said breast from lactating.

14. A method according to claim 13, wherein said protrusion is substantially the same size as said nipple.

15. A method according to claim 13, wherein said protrusion is substantially larger than said nipple.

16. A method according to claim 13, wherein the nipple-contacting surface of said protrusion is concave.

17. A method according to claim 13, wherein said support is constructed from a flexible material.

18. A method according to claim 17, wherein said flexible material is plastic.

* * * * *